United States Patent [19]

Drewes et al.

[11] Patent Number: 5,322,964
[45] Date of Patent: Jun. 21, 1994

[54] PROCESS FOR THE PREPARATION OF ALPHA-AMINOKETONE SALTS

[75] Inventors: Rolf Drewes, Lindenfels; Hans-Helmut Friedrich, Lautertal, both of Fed. Rep. of Germany

[73] Assignee: Ciba-Geigy Corporation, Ardsley, N.Y.

[21] Appl. No.: 118,107

[22] Filed: Sep. 8, 1993

[30] Foreign Application Priority Data

Sep. 10, 1992 [CH]  Switzerland .................. 2848/92

[51] Int. Cl.$^5$ ............................................ C07C 209/50
[52] U.S. Cl. .................................. 564/343; 560/41; 560/170; 564/488
[58] Field of Search .............. 564/343, 488; 560/41, 560/170

[56] References Cited

PUBLICATIONS

Ber. 35, 2998 (1902).
Chemistry and Industry (1971), 767.
Synthetic Communications 2(4), 237–242 (1972).
Chem. Pharm. Bull. 32(7), 2536–2543 (1984).
Ber. 44, 1542 (1911).
Heterocycles, vol. 29, No. 10, 1973–1982 (1989).

*Primary Examiner*—Richard L. Raymond
*Attorney, Agent, or Firm*—Luther A. R. Hall

[57] ABSTRACT

There is disclosed a process for the preparation of an alpha-aminoketone salt of formula I

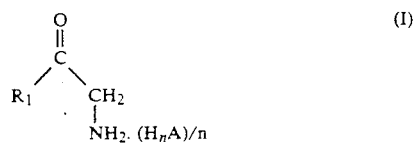

which comprises reacting a nitrosated keto ester of formula II

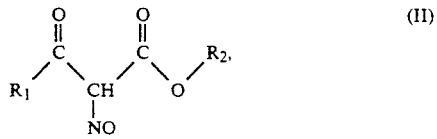

with a carboxylic anhydride of formula IV

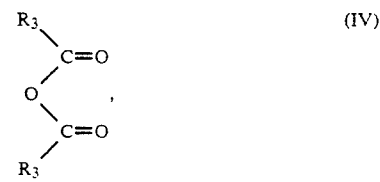

under the conditions of catalytic hydrogenation, to a compound of formula III

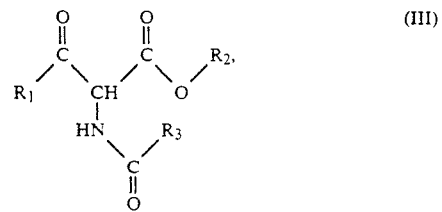

which compound of formula III is then hydrolysed with an acid $H_nA$ to the salt I, in which formulae above $R_1$ is $C_1$–$C_6$alkyl, phenoxy-$C_1$–$C_4$alkyl, phenyl, $C_7$–$C_9$phenylalkyl, or phenyl or $C_7$–$C_9$phenylalkyl which are substituted by halogen, $C_1$–$C_6$alkyl or $C_1$–$C_6$alkoxy, hydroxy or cyano, $R_2$ is $C_1$–$C_4$alkyl or cyclohexyl, n is 1 to 3, $R_3$ is $C_1$–$C_4$alkyl and A is the radical of an organic or mineral protic acid.

Pyrroles suitable as co-stabilisers for PVC can be prepared from alpha-aminoketone salts of formula I.

13 Claims, No Drawings

PROCESS FOR THE PREPARATION OF ALPHA-AMINOKETONE SALTS

The present invention relates to a process for the preparation of alpha-aminoketone salts.

Alpha-aminoketone salts, in particular phenacylamine hydrochloride, are used as educts for the synthesis of heterocyclic compounds. Pyrroles used as stabilisers for PVC can be prepared using alpha-aminoketone salts of formula I by the Knorr pyrrole synthesis [L. Knorr, H. Lange Ber. 35, 2998 (1902)].

Various processes for the preparation of alpha-aminoketone salts are known [q.v. M. Suzuki et al., Synth. Comm. 1972, 237; S. Maeda et al., Chem. Pharm. Bull. 32, 2536 (1984) C. Mannich, F. Hahn, Ber. 44, 1542 (1911)]. Some of these processes are very complicated (e.g. the urotropine process), require starting materials that are not commercially available, or they are technically extremely troublesome to carry out and are therefore of little interest economically.

Hence there is a need to provide simple and economic processes for the preparation of these products.

It has now been found that alpha-aminoketone salts can be prepared by a simple process that can also conveniently be carried out without isolation of the intermediates.

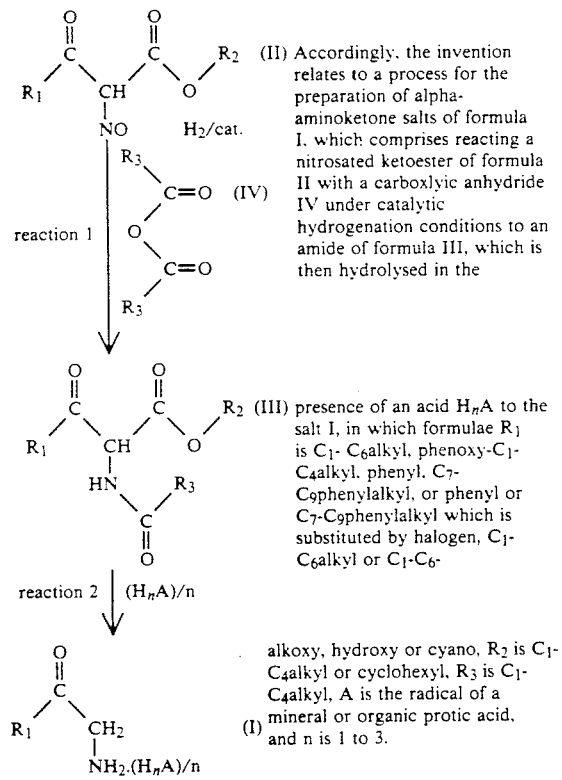

Accordingly, the invention relates to a process for the preparation of alpha-aminoketone salts of formula I, which comprises reacting a nitrosated ketoester of formula II with a carboxlyic anhydride IV under catalytic hydrogenation conditions to an amide of formula III, which is then hydrolysed in the presence of an acid $H_nA$ to the salt I, in which formulae $R_1$ is $C_1$-$C_6$alkyl, phenoxy-$C_1$-$C_4$alkyl, phenyl, $C_7$-$C_9$phenylalkyl, or phenyl or $C_7$-$C_9$phenylalkyl which is substituted by halogen, $C_1$-$C_6$alkyl or $C_1$-$C_6$-alkoxy, hydroxy or cyano, $R_2$ is $C_1$-$C_4$alkyl or cyclohexyl, $R_3$ is $C_1$-$C_4$alkyl, A is the radical of a mineral or organic protic acid, and n is 1 to 3.

$R_1$ as $C_1$-$C_6$alkyl is typically methyl, ethyl, propyl, isopropyl, n-butyl, isobutyl, tert-butyl, pentyl, isopentyl, hexyl, 2-ethylbutyl, 1-methylpentyl or 1,3-dimethylbutyl.

$R_2$ and $R_3$ as $C_1$-$C_4$alkyl have the first seven meanings as given above for $R_1$.

$C_7$-$C_9$Phenylalkyl will typically be benzyl, phenethyl, α-methylbenzyl or α,α-dimethylbenzyl.

$C_1$-$C_6$Alkoxy is typically methoxy, ethoxy, isopropoxy or hexoxy. Methoxy or ethoxy is preferred.

Phenoxy-$C_1$-$C_4$alkyl is typically phenoxymethyl, phenoxyethyl or phenoxypropyl.

Phenoxy-$C_1$-$C_4$alkyl is typically phenoxymethyl, phenoxyethyl or phenoxypropyl.

Substituted phenyl or phenylalkyl can carry one or more identical or different substituents, conveniently 1 to 3, preferably 1 or 2, substituents.

Suitable carboxylic anhydrides of formula IV are: acetic anhydride, propionic anhydride, and butyric or isobutyric anhydride. Acetic anhydride is preferred.

The first step of the process can be catalysed homogeneously or heterogeneously. Possible catalysts are:

heterogeneous catalysts: Raney nickel or Raney cobalt and preferably the noble metal catalysts on substrates commonly used for catalytic hydrogenations, preferably Pd/C, Pt/C, Ru/C, Pd-Pt/C mixed catalysts, Rh on $Al_2O_3$;

homogeneous: $[PdCl_2(CNPh)_2]$, $(NH_4)_2(IrCl_6)$/chloranilic acid. Heterogeneous catalysis on palladium, preferably palladium on carbon, is especially preferred.

The amount of catalyst is conveniently from 0.05 to 0.5% by weight, preferably 0.1 to 0.5% by weight, of noble metal, based on the compounds of formula II. The ratio of noble metal: substrate is normally from 1 to 10%.

The reactants of formulae II and IV as well as the hydrogen are conveniently used in about equimolar amounts.

The hydrogenation is preferably carried out under normal pressure and in the temperature range from typically 0°–100° C., preferably from 40° to 80° C. It can be advantageous to carry out the hydrogenation under elevated pressure, typically from 0 to 50 bar, preferably from 0 to 10 bar.

Customary solvents such as tetrahydrofuran, diethylene glycol dimethyl ether, ethyl acetate or glacial acetic acid can be used in the hydrogenation. Glacial acetic acid is preferred. It is preferred to use reactant IV as solvent.

Surprisingly, it has been found that during the acid saponification of the amide of formula II a saponification of the ester group with subsequent decarboxylation to the alpha-aminoketone occurs. The expected reaction to the amino acid ester V

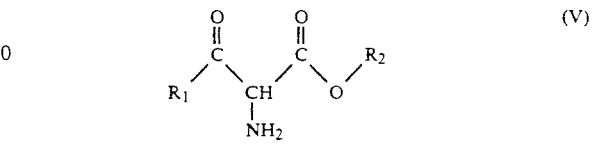

does not take place.

The saponification in the novel process (step 2) is conveniently carried out in the temperature range from 50° to 120° C., preferably from 60° to 100° C. Suitable solvents are water or the dilute acid, alcohols such as ethanol, propanol, isopropanol, ethylene glycol, ethylene glycol ether, or ethers such as ethylene glycol diethyl ether, dioxane or tetrahydrofuran.

The advantage of the process is that it is not necessary to isolate the intermediates. Heterogeneously catalysed hydrogenation is useful for this embodiment of the process.

The novel process is preferably used to prepare compounds of formula I, wherein $R_1$ is $C_1$-$C_4$alkyl, phenyl, $C_7$-$C_9$phenylalkyl, or $C_1$-$C_4$alkyl-substituted phenyl or $C_7$-$C_9$phenylalkyl, as well as those wherein $R_2$ is methyl or ethyl and $R_3$ is methyl.

The acid HA can be a mineral acid or an organic protic acid. Exemplary of such acids are HBr, HCl, $H_2SO_4$, $H_3PO_4$ and HCOOH. Hydrochloric acid or dilute sulfuric acid is preferred. Accordingly, the process is especially preferred for preparing phenacylamine hydrochloride and phenacylamine sulfate, i.e. HA in formula I is HCl or $\frac{1}{2}H_2SO_4$ and $R_1$ is phenyl.

The compounds of formula I are known and, as mentioned at the outset [q.v. also A. Alberola et al. Heterocycles 29, 1973 (1989)], can be reacted to heterocyclic compounds for a number of utilities, for example to pyrroles as disclosed in EP-A-0 390 739 and 0 465 405. It is also known that the compounds of formula I are subject to keto-enol tautomerism:

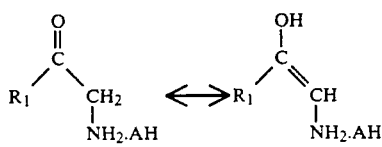

The novel process embraces the preparation of both isomers, even if for simplicity's sake formula I shows only the keto form.

The starting materials of formula Ii can be prepared from acyl acetates which are commercially available or obtainable by per se known processes by the likewise known reaction with $NaNO_2$ in acetic acid:

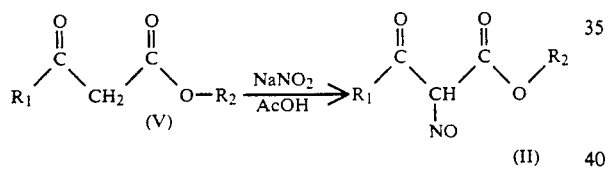

The precursor (formula V, $R_1$=phenyl, $R_2$=ethyl) of the ethyl 2-oximinobenzoylacetate used in Example 1 is commercially available. The invention is illustrated in more detail by the following non-limitative Examples in which, unless otherwise stated, parts and percentages are by weight.

EXAMPLE 1

Ethyl 2-acetamido-3-oxo-3-phenylpropionate

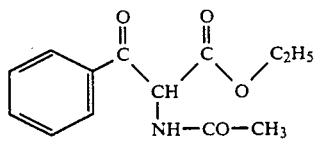

With stirring, a mixture of 221 g of ethyl 2-oximinobenzoylacetate (ethyl 2-oximino-3-oxo-3-phenylpropionate), 500 g of acetic anhydride, 50 g of glacial acetic acid and 20 g of a Pd/C catalyst (EF 101 R/W 51% $H_2O$, sold by Degussa) is hydrogenated under normal pressure at 60° C. over 4 hours. The hydrogen uptake is 40 l. Afterwards the reactor is made inert with $N_2$, flushed with nitrogen and the catalyst is removed by filtration. The filtrate is subsequently concentrated under reduced pressure on a rotary evaporator to give a residue (259.3 g), which is recrystallised from 200 ml of isopropanol/500 ml of petroleum ether.

Yield: 175.4 g (70.4% of theory) of white crystals, m.p. 81°-82° C. The mother liquor is cooled to give a further 34.5 g (13.8% of theory, m.p: 63°-64° C.; $^1$H-NMR shows a mixture of keto and enol form).

EXAMPLE 2

Phenacylamine hydrochloride

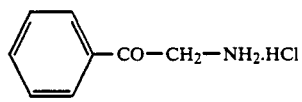

With stirring, the 259.3 g of the crude product of Example 1,375 g of concentrated hydrochloric acid and 1000 ml of water are refluxed for 3 hours. When the evolution of gas has ceased, the mixture is cooled, the turbidity is removed by filtration, and the residue is concentrated on a rotary evaporator. The residue is stirred in 250 ml of isopropanol/250 ml of tert-butyl methyl ether and cooled to 10° C. The precipitate is collected by suction filtration, washed with tert-butyl methyl ether and dried.

Yield: 132.7 g (77.5% of theory) calculated on ethyl 2-oximinobenzoylacetate used in Example 1, white crystals, m.p: 187°-88° C. (decomposition).

EXAMPLE 3

Phenacylamine hydrochloride

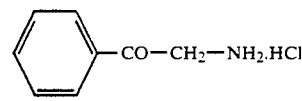

The crude product is replaced by the recrystallised ethyl 2-acetamido-3-oxo-3-phenylpropionate of Example 1 to give a yield of 92.8% of theory, m.p. 189°-91° C. (decomposition).

EXAMPLE 4

Phenacylamine sulfate

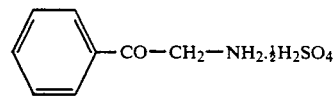

24.9 g of ethyl 2-acetamido-3-oxo-3-phenylpropionate, 7.2 g of sulfuric acid (96%) and 50 ml of water are refluxed, with stirring, for 10 hours. The reaction mixture is filtered and the filtrate is concentrated on a rotary evaporator. The crystalline residue is made into a paste with 50 ml of isopropanol, the crystals are isolated by suction filtration, washed with petroleum ether (50°-70° C.) and dried.

Yield: 12 g (65% of theory), white crystals, m.p. 152°-155° C. (decomposition).

EXAMPLE 5

1-Aminobenzylacetone hydrochloride

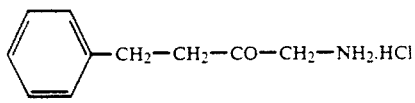

54 g of methyl 2-acetamido-3-oxo-5-phenylvalerate (60%), prepared in general accordance with the procedure described in Example 1 from methyl 2-oximino-3-oxo-5-phenylvalerate, 79 g of hydrochloric acid (32%) and 200 ml of water are refluxed, with stirring, for 2 hours. The 2-phase reaction mixture is then concentrated on a rotary evaporator. The partially crystalline residue is dissolved in 100 ml of warm isopropanol and to the solution are added 30 ml of tert-butyl methyl ether. After cooling, the precipitated crystals are isolated.

Yield: 16.8 g (68% of theory, calculated on 100% of methyl 2-acetamido-3-oxo-5-phenylvalerate, white crystals from isopropanol, m.p. 152° C. (decomposition).

EXAMPLE 6

Aminoacetone hydrochlorid:
$CH_3-CO-CH_2-NH_2.HCl$ 35 g of ethyl 2-acetamido-3-oxo-butyrate, prepared in general accordance with the procedure described in Example 1 from methyl 2-oximino-3-oxo-butyrate 68 g of hydrochloric acid (32%) and 180 ml of water are stirred for 3 h at 60°–70° C. After $CO_2$ evolution has ceased, the reaction mixture is concentrated.

Yield: 20.3 g of a reddish brown viscous liquid. $n_D^{30}$: 1.488

What is claimed is:

1. A process for the preparation of an alpha-aminoketone salt of formula I

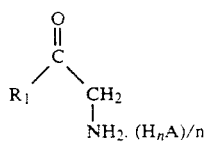

which comprises reacting a nitrosated keto ester of formula II

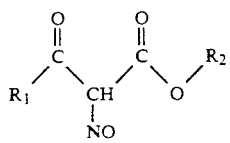

with a carboxylic anhydride of formula IV

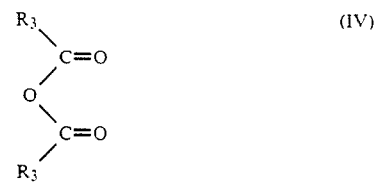

under the conditions of catalytic hydrogenation, to a compound of formula III

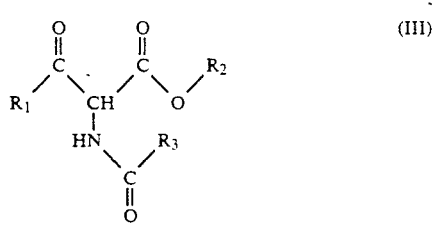

which compound of formula III is then hydrolysed with an acid $H_nA$ to the salt I, in which formulae above $R_1$ is $C_1$-$C_6$alkyl, phenoxy-$C_1$-$C_4$alkyl, phenyl, $C_7$-$C_9$phenylalkyl, or phenyl or $C_7$-$C_9$phenylalkyl which are substituted by halogen, $C_1$-$C_6$alkyl or $C_1$-$C_6$alkoxy, hydroxy or cyano, $R_2$ is $C_1$-$C_4$alkyl or cyclohexyl, n is 1 to 3, $R_3$ is $C_1$-$C_4$alkyl and A is the radical of an organic or mineral protic acid.

2. A process according to claim 1, wherein $R_1$ is $C_1$-$C_4$alkyl, phenyl, $C_7$-$C_9$phenylalkyl or $C_1$-$C_4$alkyl-substituted phenyl or $C_7$-$C_9$phenylalkyl.

3. A process according to claim 1, wherein $R_2$ is methyl or ethyl and $R_3$ is methyl.

4. A process according to claim 1, which is carried out without isolation of intermediates.

5. A process according to claim 1, wherein the catalytic hydrogenation is carried out in the presence of a palladium on carbon catalyst.

6. A process according to claim 1, wherein the acid $H_nA$ is selected from the group consisting of HBr, HCl, $H_2SO_4$, $H_3PO_4$ and HCOOH.

7. A process according to claim 1, wherein the acid $H_nA$ is HCl or ½ $H_2SO_4$.

8. A process according to claim 1, wherein the compound of formula I is phenacylamine hydrochloride or phenacylamine sulfate.

9. A process according to claim 1, wherein the pressure during the hydrogenation is from 0 to 50 bar.

10. A process according to claim 1, wherein the temperature during the hydrogenation is from 0° to 100° C.

11. A process according to claim 1, wherein the the pressure during the hydrogenation is from 0 to 10 bar.

12. A process according to claim 1, wherein the temperature during the hydrogenation is from 40° to 80° C.

13. A process according to claim 1, wherein the temperature during the hydrolysis is from 50° to 120° C.

* * * * *